United States Patent [19]

Cimarusti et al.

[11] 4,237,128

[45] Dec. 2, 1980

[54] 7-[2-(2-AMINO-4-THIAZOLYL)-2-[(1-CAR-BOXY-1,1-DIALKYL)ALKOX-YIMINO]ACETAMIDO]CEPHEM SULFOXIDES

[75] Inventors: Christopher M. Cimarusti, Hamilton; William H. Koster, East Amwell Township, Hunterdon County; Richard B. Sykes, Rocky Hill, all of N.J.

[73] Assignee: E. R. Squibb & Sons, Inc., Princeton, N.J.

[21] Appl. No.: 29,417

[22] Filed: Apr. 12, 1979

[51] Int. Cl.$^3$ .................. A61K 31/545; C07D 501/34
[52] U.S. Cl. ..................................... 424/246; 544/21; 544/22; 544/23; 544/25; 544/27; 544/28
[58] Field of Search ........................... 424/246; 544/28

[56] References Cited

U.S. PATENT DOCUMENTS

| 3,641,014 | 2/1972 | Murphy et al. ................. 546/30 |
| 3,971,778 | 7/1976 | Cook et al. .................... 424/246 |
| 4,075,337 | 2/1978 | Marx et al. .................... 424/246 |
| 4,084,049 | 4/1978 | Kamiya et al. ................ 424/246 |
| 4,091,209 | 5/1978 | Cook et al. .................... 424/246 |
| 4,098,888 | 7/1978 | Ochiai et al. .................. 544/28 |
| 4,138,555 | 2/1979 | Cook et al. .................... 424/246 |
| 4,144,393 | 3/1979 | Bradshaw et al. .............. 544/28 |

FOREIGN PATENT DOCUMENTS 2812625  9/1978  Fed. Rep. of Germany .
2716677 10/1978  Fed. Rep. of Germany .

OTHER PUBLICATIONS

*Elks, "Recent Advances in the Chemistry of β-Lactam Antibiotics", from J. J. de Konig et al., Stereospecific Synthesis of Biologically Active Cephalosporin R-Sulfoxides, (1977), pp. 161-166.

*Primary Examiner*—Paul M. Coughlan, Jr.
*Attorney, Agent, or Firm*—Lawrence S. Levinson; Stephen B. Davis

[57] ABSTRACT

Compounds of the formula

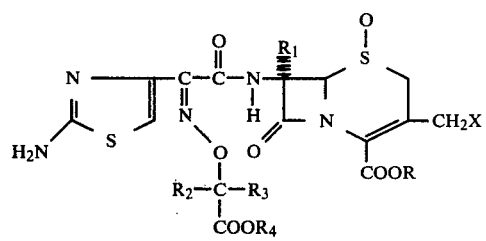

wherein R is hydrogen, sodium, potassium, or certain ester groups; $R_1$ is in the α-configuration and is hydrogen or methoxy; $R_2$ and $R_3$ are independently selected from methyl, ethyl, i-propyl, and n-propyl; $R_4$ is hydrogen, sodium, potassium or certain ester groups, and X is hydrogen,

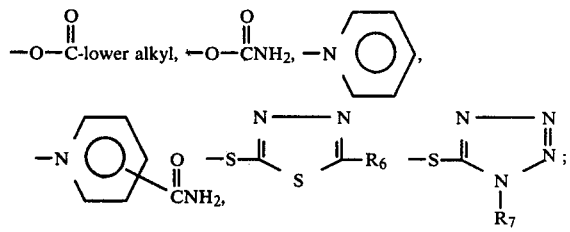

$R_6$ is hydrogen or lower alkyl; $R_7$ is hydrogen, lower alkyl,

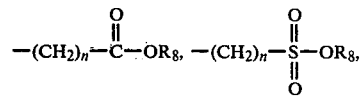

or —$(CH_2)_n$-N-(lower alkyl)$_2$; $R_8$ is hydrogen, sodium or potassium; n is an integer from 1 to 4; are disclosed. These compounds are useful as antibacterial agents.

5 Claims, No Drawings

7-[2-(2-AMINO-4-THIAZOLYL)-2-[(1-CARBOXY-1,1-DIALKYL)ALKOXYIMINO]ACETAMIDO]-CEPHEM SULFOXIDES

BACKGROUND OF THE INVENTION

Hoechst in German Offenlegungsschrift No. 2,716,677 discloses α- and β-sulfoxides of the formula

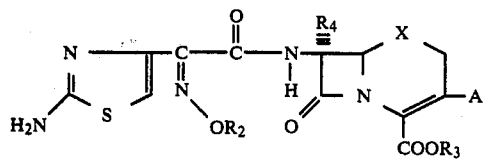

wherein X is the sulfoxide group, $R_3$ is hydrogen, A is various 3-position substituents and $R_2$ is defined as alkyl of 1 to 4 carbons, for example methyl, having one or more substituents such as for example alkyl of 1 to 4 carbons, carboxy, etc. Numerous groups are described in the tables under the heading $R_2$ including

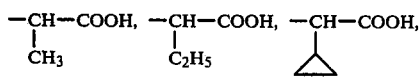

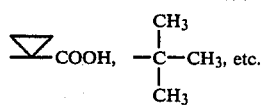

Roussel-Uclaf in German Offenlegungsschrift No. 2,812,625 discloses cephalosporins of the formula

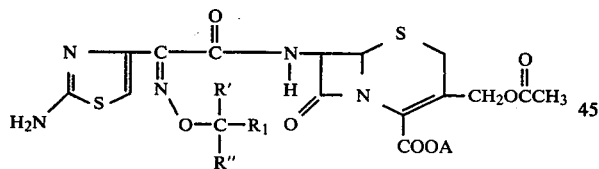

wherein A is hydrogen, alkali metal, etc., R' and R" are hydrogen or alkyl of 1 to 3 carbons, and $R_1$ is $—CO_2R_1'$ wherein $R_1'$ is hydrogen, alkyl of 1 to 3 carbons, alkali metal, etc. Example 14 discloses the compound wherein R' and R" are both methyl and A and $R_1'$ are both sodium.

Marx et al. in U.S. Pat. No. 4,075,337 disclose the preparation of antibacterially active cephalosporin sulfoxides.

Cook et al. in U.S. Pat. Nos. 3,971,778 and 4,138,555 disclose the preparation of additional antibacterially active cephalosporin sulfoxides.

SUMMARY OF THE INVENTION

This invention is directed to cephalosporins of the formula

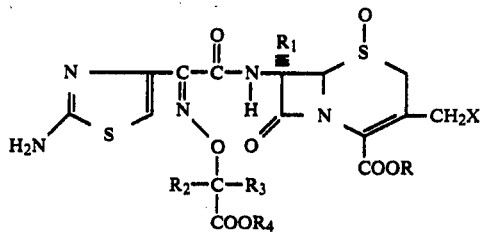

R represents hydrogen, sodium, potassium, benzyl, p-methoxybenzyl, diphenylmethyl, t-butyl, $—CH_2—O—$lower alkyl,

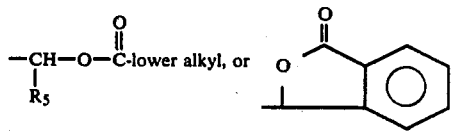

$R_1$ is in the α-configuration and is hydrogen or methoxy.

$R_2$ and $R_3$ are independently selected from methyl, ethyl, n-propyl and i-propyl.

$R_4$ is hydrogen, sodium, potassium, $—CH_2—O—$lower alkyl,

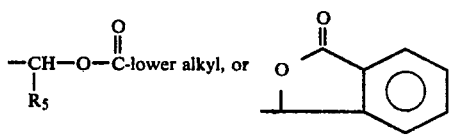

$R_5$ is hydrogen or lower alkyl.
X is hydrogen,

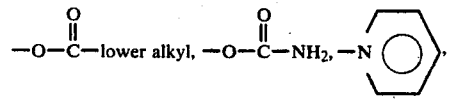

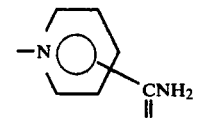

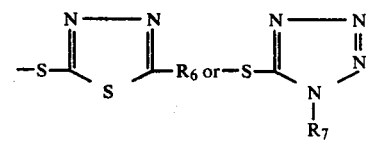

$R_6$ is hydrogen or lower alkyl.
$R_7$ is hydrogen, lower alkyl,

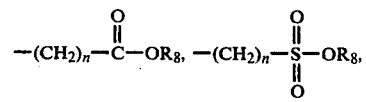

or $—(CH_2)_n—N—$(lower alkyl)$_2$.
$R_8$ is hydrogen, sodium, or potassium.
n represents an integer from 1 to 4.

When X is pyridinium or carbamoyl substituted pyridinium, the compounds can be structurally represented as having the formula

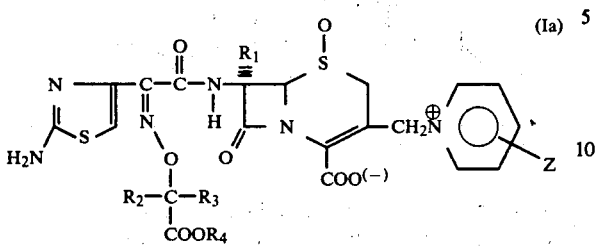

wherein Z is hydrogen or carbamoyl.

DETAILED DESCRIPTION OF THE INVENTION

The lower alkyl groups referred to throughout this specification include straight or branched chain hydrocarbon groups containing 1 to 4 carbons, e.g., methyl, ethyl, i-propyl, t-butyl, etc.

The compounds of formula I and their intermediates that are described below that have the 2-amino-4-thiazolyl group as part of their structure are, of course, tautomeric and can also be structurally represented as containing a 2-imino group. Thus, the compounds of formula I can be represented as

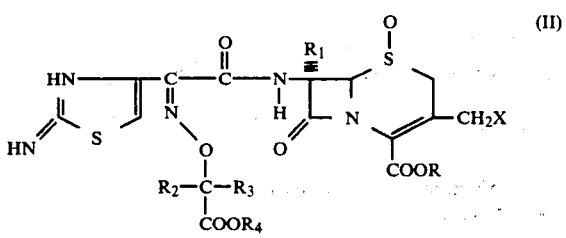

The intermediates and final products are being structurally represented and named throughout this specification as 2-amino-4-thiazoles though both forms are within the scope of the invention.

The compounds of formula I and the intermediates described below having the imino substituent

can be obtained as the syn or anti isomer or as a mixture of isomers. All of these isomeric forms are within the scope of this invention. However, in general, it is preferred to obtain the final products in the syn form since that isomeric form has the greatest activity.

The symbol

is being used to represent that the sulfoxides of formula I and in the various intermediates described below can be in either the α- or β-configuration. When the sulfoxide is only in the β-configuration it will be represented as

and when it is only in the α-configuration it will be represented as

The compounds of formula I can be prepared by several methods depending upon the configuration of the sulfoxide group and the 3-position substituent.

For example, the β-sulfoxides of formula I can be prepared by the direct oxidation of the corresponding sulfide compound. Thus, a cephalosporin of the formula

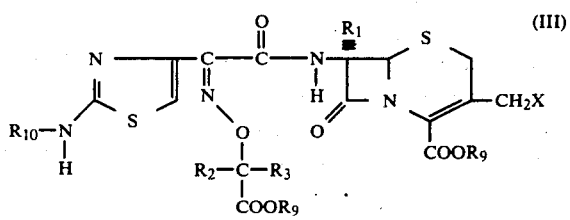

wherein X, $R_1$, $R_2$ and $R_3$ are as defined above, each $R_9$ is independently selected from hydrogen and an acid removable ester protecting group such as benzyl, diphenylmethyl, p-methoxybenzyl, and t-butyl, and $R_{10}$ is hydrogen, hydrogen protected with its trifluoroacetate salt, or an acid removable protecting group such as t-butoxycarbonyl or formyl; is oxidized with a percarboxylic acid such as m-chloroperbenzoic acid, peracetic acid, etc., at from about 0° to about 25° C.

The sulfide cephalosporins of formula III are disclosed in various references including German Offenlegungsschrift Nos. 2,812,625 and 2,714,880. These sulfide cephalosporins can be prepared by various methods. For example, the cephalosporins of formula III when X is hydrogen,

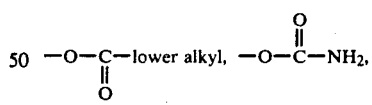

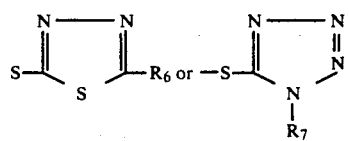

can be prepared by acylating an ester of the formula

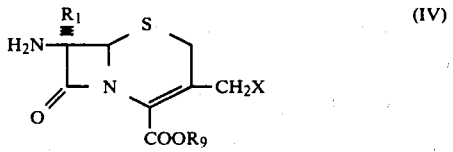

with the trityl protected compound of the formula

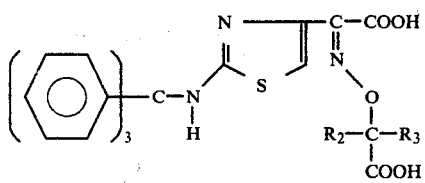 (V)

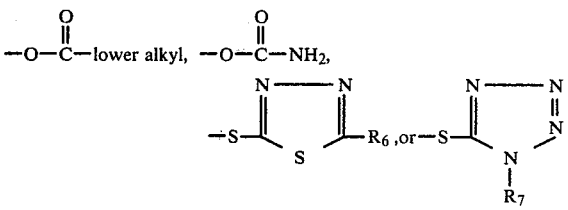

to yield the intermediate of the formula

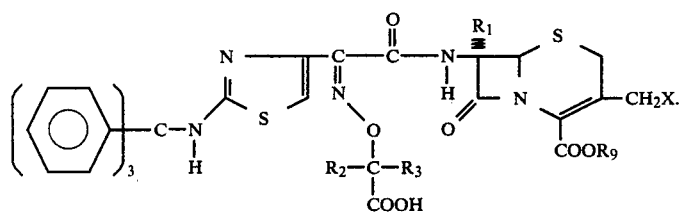 (VI)

The acylation reaction is carried out in the presence of a coupling agent such as dicyclohexylcarbodiimide.

The intermediate of formula VI is then treated to remove the trityl and $R_9$ ester protecting groups and yield the compounds of formula III in the acid form. Preferably, in the above reactions, $R_9$ is t-butyl and the intermediate of formula VI is treated with trifluoroacetic acid and anisole to remove the trityl and t-butyl protecting groups and yield the trifluoroacetic acid salt of the compound of formula III.

The trityl protected compound of formula V can be prepared by reacting a hydroxyimino compound of the formula

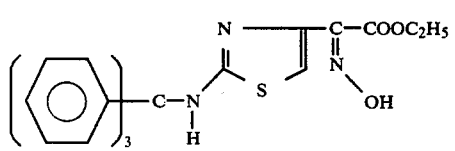 (VII)

with a compound of the formula

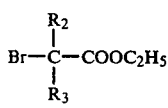 (VIII)

in the presence of base such as potassium carbonate to yield the compound of the formula

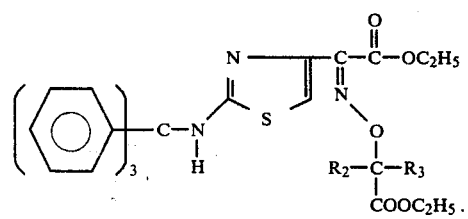 (IX)

This intermediate is then treated with sodium hydroxide to yield the acid of formula V.

The sulfide cephalosporins of formula III wherein X is hydrogen, can also be prepared by acylating an ester of formula IV with a formyl protected compound of the formula (X)

to yield the intermediate of the formula (XI)

The acylation reaction can be performed directly with the acid of formula X by use of a coupling agent such as dicyclohexylcarbodiimide. Alternatively, the acid compound of formula X can be converted to an activated derivative such as the acid chloride or bromide, an anhydride, mixed anhydride, or an activated ester formed according to methods known in the art.

The intermediate of formula XI is then treated with hydrochloric acid to remove the formyl protecting group and yield the sulfide cephalosporin of formula III. Alternatively, the compound of formula X can be treated with hydrochloric acid to remove the formyl group prior to the acylation reaction thereby producing the sulfides of formula III directly.

The formyl protected compound of formula X is prepared by reacting an O-substituted hydroxylamine of the formula

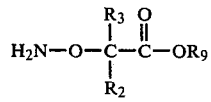 (XII)

with the thiazole of the formula

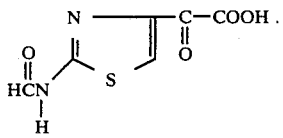 (XIII)

The hydroxylamine of formula XII can be prepared by reacting N-hydroxyphthalimide with the bromoacetate of the formula

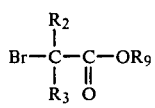 (XIV)

in the presence of base such as potassium carbonate to yield the compound of the formula

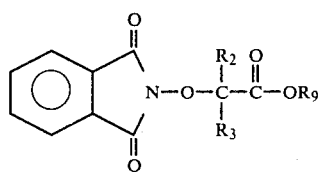 (XV)

which is then treated with hydrazine hydrate.

The sulfide compounds of formula III wherein X is

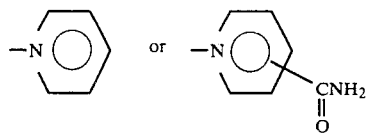

are prepared by reacting a compound of formula III wherein R is hydrogen and X is

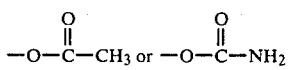

with pyridine or carbamoyl substituted pyridine in a polar solvent such as water and in the presence of a catalyst such as an alkali metal thiocyanate according to the procedures taught in U.S. Pat. No. 3,792,047 and German Offenlegungsschrift No. 2,234,280.

Also, the compounds of formula III wherein X is heterothio

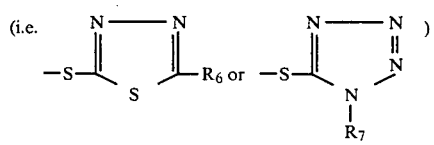

can be prepared by reacting the compound of formula III wherein R is hydrogen and X is

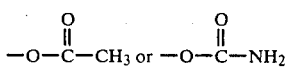

with a mercaptan of the formula hetero-S-H (XVI)

or an alkali metal (preferably sodium) mercaptan salt of the formula hetero-S-alkali metal (XVII)

Such methods of introducing a heterothio group in the 3-position are disclosed in various U.S. Pat. Nos. including 3,955,213, 4,066,762, etc.

The α- and β-sulfoxides of formula I wherein X is hydrogen,

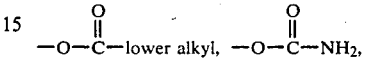

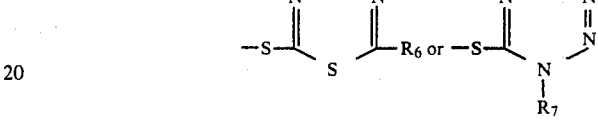

can be prepared by the acylation of 7-amino cephalosporanic acid ester sulfoxide of the formula

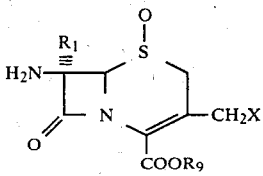 (XVIII)

with an activated derivative of the acid of the formula

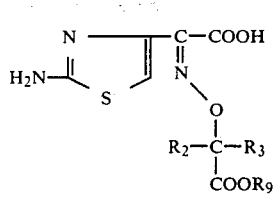 (XIX)

in the presence of a coupling agent such as dicyclohexylcarbodiimide to yield the ester of the formula

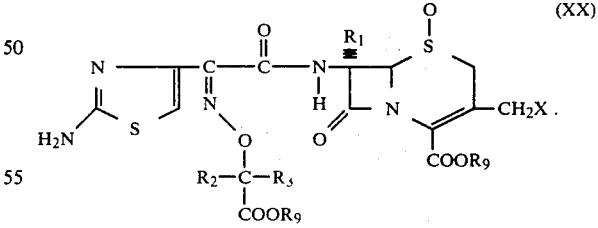 (XX)

Removal of the ester protecting groups such as by treatment with trifluoroacetic acid and anisole to yield the corresponding trifluoroacetic acid salt which can then be converted into the free acid of formula I.

The preferred activated derivative of formula XIX is the N-hydroxybenzotriazole obtained by treating the acid of formula XIX with N-hydroxybenzotriazole and dicyclohexylcarbodiimide.

The 7-amino cephalosporanic acid ester α- and β-sulfoxides of formula XVIII are prepared by converting the 7-amino cephalosporanic acid starting material to the Schiff base ester of the formula

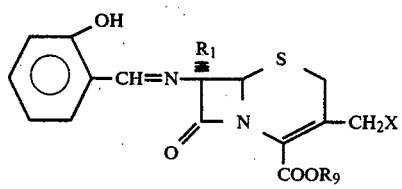 (XXI)

which is then oxidized with a percarboxylic acid such as m-chloroperbenzoic acid to yield a mixture of α- and β-sulfoxide Schiff base cephalosporin esters. The Schiff base sidechain is cleaved by treatment with toluenesulfonic acid and α- and β-sulfoxide 7-amino cephalosporanic acid esters are separated chromatographically.

The α- and β-sulfoxides of formula Ia can be prepared by reacting a compound of formula I wherein R is hydrogen and X is

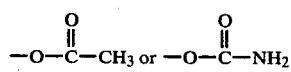

with pyridine or carbamoyl substituted pyridine in a polar solvent such as water and in the presence of a catalyst such as an alkali metal thiocyanate as described above.

Also, the α- and β-sulfoxides of formula I wherein X is heterothio can be prepared by reacting the compound of formula I wherein R is hydrogen and X is

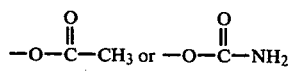

with the mercaptan of formula XVI or the alkali metal mercaptan salt of formula XVII as described above.

The compounds of formula I wherein R, R₄, and R₈ are sodium or potassium are prepared by reacting the corresponding free acid of formula I (R, R₄ and R₈ are hydrogen) with the appropriate salt forming ion.

The compounds of formula I wherein R and R₄ are

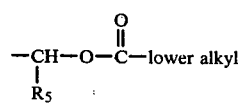

can be obtained by treating the corresponding free acid of formula I with two moles of a compound of the formula

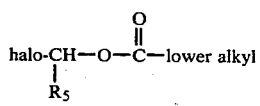 (XXII)

wherein halo is chlorine or bromine in an inert solvent such as dimethylformamide at or below ambient temperature.

Similarly, the compounds of formula I wherein R and R₄ are

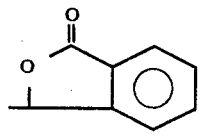

are prepared by treating the free acid compound of formula I with a compound of the formula

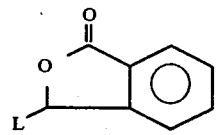 (XXIII)

wherein L is hydroxy or Br as taught in U.S. Pat. Nos. 3,860,579, 3,951,954, and 4,072,677.

Preferred compounds of this invention are those of formula I wherein R is hydrogen, sodium or potassium; R₁ is hydrogen; R₂ and R₃ are both methyl; R₄ is hydrogen, sodium, or potassium; X is hydrogen,

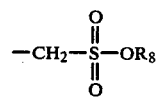

R₇ is hydrogen, methyl, —CH₂—COOR₈,

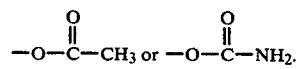

or —(CH₂)₂—N(CH₃)₂; and R₈ is hydrogen, sodium or potassium.

Most preferred are the above compounds wherein X is $$-O-\overset{O}{\underset{\|}{C}}-CH_3 \text{ or } -O-\overset{O}{\underset{\|}{C}}-NH_2.$$

The compounds of formula I wherein R and R₄ are hydrogen, sodium, potassium, —CH₂—O—lower alkyl,

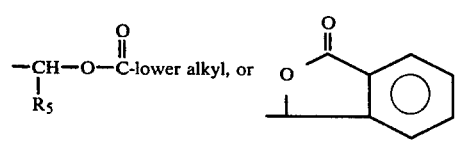

are useful antibacterial agents possessing activity against various gram-negative organisms including Klebsiella, Proteus, Enterobacter, and Pseudomonas species. They may be used as antibacterial agents to combat infections due to organisms such as those named above, and in general may be utilized in a manner similar to gentamicin and other gram-negative antibacterial agents. For example, a compound of formula I or a physiologically acceptable salt thereof may be used in various animal species in an amount of about 1 to 100 mg/kg, daily in parenteral form, in single or two to four divided doses to treat infections of bacterial origin, e.g., 5.0 mg/kg in mice.

Up to about 600 mg. of an acid compound of formula I or a physiologically acceptable salt or ester thereof may be incorporated in an injectable form prepared according to conventional pharmaceutical practice.

In particular, the most preferred compounds of formula I (i.e., those wherein R and $R_4$ are hydrogen, sodium or potassium, $R_1$ is hydrogen; $R_2$ and $R_3$ are both methyl; and X is

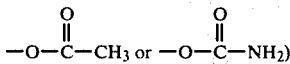

exhibit exceptional activity against strains of *Pseudomonas aeruginosa*.

Illustrative process details are in the examples for the various reactions. All temperatures are on the centigrade scale.

EXAMPLE 1

[5S-[5α,6β,7α(Z)]]-3-[(Acetyloxy)methyl]-7-[[(2-amino-4-thiazolyl)[(1-carboxy-1-methylethoxy)imino]acetyl]amino]-8-oxo-5-thia-1-azabicyclo[4.2.0]oct-2-ene-2-carboxylic acid, 5-oxide, disodium salt (i.e. β-sulfoxide, syn isomer)

(a) Ethyl 2-[(1-ethoxycarbonyl-1-methylethoxy)imino-2-(2-tritylaminothiazol-4-yl)]acetate (syn isomer)

3 g. (6.56 mmol.) of ethyl 2-hydroxyimino-2-(2-tritylaminothiazol-4-yl)acetate (syn isomer), prepared according to the procedure described in Belgian Patent 852,971, 0.91 g. (6.56 mmol.) of potassium carbonate, and 1.28 g. (6.56 mmol.) of ethyl bromoisobutyrate are dissolved in 30 ml. of dry dimethylformamide and stirred at room temperature for 18 hours. The mixture is poured into 1000 ml. of water, extracted with EtOAc (twice), and the combined extracts are washed with water, then with saturated sodium chloride solution, and dried ($Na_2SO_4$). The solvent is removed in vacuo and the residue is chromatographed on silica gel. Elution with 5–10% EtOAc in $CH_2Cl_2$ gives crude product as an oil. Crystallization from ether-pentane yields 2.65 g. of ethyl 2-[(1-ethoxycarbonyl-1-methylethoxy)imino-2-(2-tritylaminothiazol-4-yl)]acetate (syn isomer); m.p. 120°–122°.

(b) 2-[(1-Carboxy-1-methylethoxy)imino-2-(2-tritylaminothiazol-4-yl)]acetic acid (syn isomer)

A mixture of 2.61 g. (4.56 mmol.) of ethyl 2-[(1-ethoxycarbonyl-1-methylethoxy)imino-2-(2-tritylaminothiazol-4-yl)]acetate (syn isomer), from part (a), and 5 ml. of 1.84 N sodium hydroxide solution in 25 ml. of ethanol is stirred for four days at room temperature. After removing the solvent in vacuo, the residue is taken up in ethyl acetate-water, shaken, and the organic layer is discarded. The aqueous solution is layered with EtOAc and adjusted to pH 2.7 with 1 N HCl. The acidic layer is extracted several times with EtOAc, the extracts are combined, washed with saturated sodium chloride solution, and dried ($Na_2SO_4$).

The solvent is removed in vacuo and the residue is precipitated from a methylene chloride-ether-pentane mixture yielding as a colorless powder 2.37 g. of 2-[(1-carboxy-1-methylethoxy)imino-2-(2-tritylaminothiazol-4-yl)]acetic acid (syn isomer): NMR ($CDCl_3$-$CD_3OD$) δ1.58 (s,6H), 6.7 (s,1H), 7.32 (s,15H).

(c) [6R-[6α,7β(Z)]]-3-[(Acetyoxy)methyl]-7-[[(2-tritylamino-4-thiazolyl)[(1-carboxyl-1-methylethoxy)imino]acetyl]amino]-8-oxo-5-thia-1-azabicyclo[4.2.0]oct-2-ene-2-carboxylic acid, t-butyl ester 2 g. (3.88 mmol.) of the acetic acid product from part (b) and 0.8 g. (3.88 mmol.) of dicyclohexylcarbodiimide are stirred for 10 minutes in 30 ml. of dry methylene chloride. Afterward, 1.27 g. (3.88 mmol.) of 7-aminocephalosporanic acid, t-butyl ester is added and the mixture is stirred for 4.5 hours at room temperature. After filtering, the solvent is removed in vacuo and the residue is chromatographed on silica gel. Eluting with 98:2 methylene chloride:methanol yields 1.02 g. of crude product. Further purification by chromatography on silica gel TLC plates developed in 9:1 chloroform:methanol yields 0.8 g. of [6R-[6α,7β(Z)]]-3-[(acetyloxy)methyl]-7-[[(2-tritylamino-4-thiazolyl)[(1-carboxy-1-methylethoxy)imino]acetyl]amino]-8-oxo-5-thia-1-azabicyclo[4.2.0]oct-2-ene-2-carboxylic acid, t-butyl ester: NMR ($CDCl_3$-$CD_3OD$) δ1.53 (m,15H), 2.03 (s,3H), 4.83 (ABq, J=14Hz,2H), 5.0 (d,J=5Hz,1H), 5.87 (d,J=5Hz,1H), 6.63 (s,H), 7.23 (s,15H): IR($CHCl_3$) 1790, 1740, 1725, 1680 $cm^{-1}$.

(d) [6R-[6α,7β(Z)]]-3-[(Acetyloxy)methyl]-7-[[(2-amino-4-thiazolyl)[(1-carboxy-1-methylethoxy)imino]acetyl]amino]-8-oxo-5-thia-1-azabicyclo[4.2.0]oct-2-ene-2-carboxylic acid, trifluoroacetate salt 0.4 g. (0.451 mmol.) of the t-butyl ester product from part (c) and 0.45 ml. of anisole are combined, cooled in an ice bath, and treated with 10 ml. of trifluoroacetic acid. The mixture is swirled until all the solid is dissolved. After standing in the ice-bath for four hours, the solvent is removed in vacuo and residual trifluoroacetic acid is removed by co-distillation with benzene under reduced pressure. Trituration with ether yields, as an amorphous powder, 0.165 g. of [6R-[6α,7β(Z)]]-3-[(acetyloxy)methyl]-7-[[(2-amino-4-thiazolyl)[(1-carboxy-1-methylethoxy)imino]acetyl]amino]-8-oxo-5-thia-1-azabicyclo[4.2.0]oct-2-ene-2-carboxylic acid, trifluoroacetate salt: $R_f$ 0.38 (silica gel, 3:1:1 n-butanol:acetic acid:water); NMR ($CDCl_3$-$CD_3$-$CD_3OD$) δ1.65 (s,6H), 2.07 (s,3H), 6.95 (s,1H); IR (KBr) 3400, 2500 (sh), 1780, 1728, 1675 $cm^{-1}$.

(e) [5S-(5α,6β,7α(Z))]-3-[(Acetyloxy)methyl]-7-[[(2-amino-4-thiazolyl)[(1-carboxy-1-methylethoxy)imino]acetyl]amino]-8-oxo-5-thia-1-azabicyclo[4.2.0]oct-2-ene-2-carboxylic acid, 5-oxide, trifluoroacetate salt The trifluoroacetate salt (100 mg.) from part (d) is suspended in dry $CH_2CL_2$ (2 ml.) under a nitrogen atmosphere. The mixture is cooled in an ice bath and trifluoroacetic acid (1 ml.) is added causing dissolution of the solid. Then m-chloroperbenzoic acid (32 mg., 85% pure) is added and, after stirring for 2.5 hours at 0°–5°, the solvent is removed in vacuo. Trituration of the residue three times with ether yields as a yellow 84 mg. of [5-S-[5α,6β,7α(Z)]]-3-[(acetyloxy)methyl]-7-[[(2-amino-4-thiazolyl)[(1-carboxy-1-methylethoxy)imino]acetyl]amino]-8-oxo-5-thia-1-azabicyclo[4.2.0]oct-2-ene-2-carboxylic acid, 5-oxide, trifluoroacetate salt: NMR (CDCl$_3$-CD$_3$OD) δ1.65 (s, C(CH$_3$)$_2$, 2.07 (s,CH$_3$), 6.03 (d, J=5H$_z$, H$_7$), 7.0 (s, thiazole H); IR(KBr) 1790, 1730, 1675, 1630, 1520 cm$^{-1}$.

(f)
[5S-[5α,6β,7α(Z)]]-3-[(Acetyloxy)methyl]-7-[[(2-amino-4-thiazolyl)[(1-carboxy-1-methylethoxy)imino]acetyl]amino]-8-oxo-5-thia-1-azabicyclo[4.2.0]-oct-2-ene-carboxylic acid, 5-oxide, disodium salt The trifluoroacetate salt product from part (e) is dissolved in a mixture of methanol and ethanol. Three molar equivalents of sodium bicarbonate is added and the desired disodium salt is precipitated by the addition of acetone-ether.

EXAMPLE 2
[5S-[5α,6β,7α(Z)]]-7-[[(2-Amino-4-thiazolyl)[(1-carboxy-1-methylethoxy)imino]acetyl]amino]-3-[[(1-methyl-1H-tetrazol-5-yl)thio]methyl]-8-oxo-5-thia-1-azabicyclo[4.2.0]oct-2-ene-2-carboxylic acid, 5-oxide, disodium salt (i.e. β-sulfoxide, syn isomer)

(a) Diphenylmethyl bromoisobutyrate

Diphenyldiazomethane (33.76 g., 0.173 mole) in 150 ml. of dichloromethane is added slowly over the period of about an hour to a solution of bromoisobutyric acid (28.91 g., 0.173 mole) in 300 ml. of dichloromethane. The resulting mixture is stirred for about 17 hours at room temperature and the solvents are removed in vacuo. The residue solidifies upon standing under reduced pressure to yield 55.43 g. of diphenylmethyl bromoisobutyrate.

(b)
(1-Diphenylmethoxycarbonyl-1-methylethoxy)phthalimide

Potassium carbonate (22.9 g., 0.166 mole) is added to a mixture of the ester from part (a) (55.43 g., 0.166 mole) and N-hydroxyphthalimide (27.13 g., 0.166 mole) in 270 ml. of dry dimethylformamide. The viscous reaction mixture is stirred with an overhead stirrer for three days and becomes a deep red-brown color.
The reaction mixture is then poured into water slowly with stirring and a white solid forms which is filtered after 30 minutes. The precipitate is collected, dissolved in dichloromethane, washed with water, dried, filtered, and concentrated in vacuo to a small volume. The crystals that form are collected and dried over P$_2$O$_5$ in vacuo to yield 53.82 g. of (1-diphenylmethoxycarbonyl-1-methylethoxy)phthalamide.

(c)
(1-Diphenylmethoxycarbonyl-1-methylethoxy)amine

Hydrazine hydrate (99%, 12.62 ml., 0.26 mole) is added to a solution of the phthalimide from part (b) (53.82 g., 0.13 mole) in 500 ml. of dichloromethane. Heat evolves from the reaction mixture and a tacky solid precipitates. After stirring for three hours, the solid is collected and washed with dichloromethane. The organic extracts are washed with dilute NH$_4$OH, then with water, dried with MgSO$_4$ (copious amounts), filtered, and concentrated in vacuo to yield 41 g. of white crystalline solid (1-diphenylmethoxycarbonyl-1-methylethoxy)amine.

(d)
2-(1-Diphenylmethoxycarbonyl-1-methylethoxy)imino-2-(2-formamido-4-thiazolyl)acetic acid (2-Formamido-4-thiazolyl)glyoxylic acid (2 g., 0.01 mole), prepared according to the procedure described in Belgian Patent 855,593, is added to a solution of the amine from part (c) (2 g., 0.01 mole) in 150 ml. of ethanol. The mixture is refluxed for 17 hours and a solid precipitates. After cooling, the mixture is filtered to yield 1.7 g. of 2-(1-diphenylmethoxycarbonyl-1-methylethoxy)imino-2-(2-formamido-4-thiazolyl)acetic acid as a powder. Concentration of the filtrate yields an additional 2.32 g. of product.

(e)
2-(2-Amino-4-thiazolyl)-2-(1-diphenylmethoxycarbonyl-1-methylethoxy)iminoacetic acid, hydrochloride salt.

Concentrated hydrochloric acid (403 μl., 4.84 mmol.) is added to a suspension of the product from part (d) (1.7 g., 3.64 mmol.) in dry methanol. The suspended material dissolves immediately and the reaction mixture is stirred for four hours. The solvent is removed under reduced pressure yielding as a residue 2-(2-amino-4-thiazolyl)-2-(1-diphenylmethoxycarbonyl-1-methylethoxy)imino acetic acid, hydrochloride salt: NMR (CDCl$_3$-CD$_3$OD) δ 1.70 (s,6H,CH$_3$), 6.93 (s, 1H, thiazole H), 7.02 (s, 1H, CHO), 7.33 (s, 10H, aromatic H).

(f)
2-(2-Amino-4-thiazolyl)-2-(1-diphenylmethoxycarbonyl-1-methylethoxy)iminoacetic acid A suspension of the hydrochloride salt product from part (e) in water (20 ml./g.) is adjusted to pH 2.6 and stirred for 30 minutes at 0°. The resulting suspension is filtered, washed thoroughly with water, and dried to yield 2-(2-amino-4-thiazolyl)-2-(1-diphenylmethoxycarbonyl-1-methylethoxy)iminoacetic acid.

(g)
[6R-[6α,7β(Z)]]-7-[[(2-Amino-4-thiazolyl)[(1-diphenylmethoxycarbonyl-1-methylethoxy)imino]acetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester To a solution of the acid product from part (f) (941 mg., 2.14 mmol.) in 23 ml. of dimethylformamide is added N-hydroxybenzotriazole (328 mg., 2.14 mmol.), dicyclohexylcarbodiimide (486 mg., 2.14 mmol.) and 7-amino-3-[[(1-methyl-1H-tetrazol-5-yl)thio]methyl]-8-oxo-5-thia-1-azabicyclo[4.2.0]oct-2-ene-2-carboxylic acid, diphenylmethyl ester (1.06 g., 2.14 mmol.). The mixture is stirred for five minutes at 0° and three hours at room temperature under a nitrogen atmosphere. The resulting mixture is filtered to remove urea. The filtrate is concentrated to about 2 ml. at less than 40°, diluted with 340 ml. of ethyl acetate, washed three times with 340 ml. of 0.5 N HCl, washed once with 230 ml. of water, washed twice with 230 ml. of 5% NaHCO$_3$, dried over Na$_2$SO$_4$ and filtered. The filtrate is evaporated in vacuo to yield 2.13 g. of crude product. This material is purified (300 ml. silica gel column, 50%

EtOAc in CHCl3 as eluant) to yield 1.17 g. of [6R-[6 α,7β(Z)]]-7-[[(2-amino-4-thiazolyl)[(1-diphenylmethoxycarbonyl-1-methylethoxy)imino]acetyl]amino]-3-[[(1-methyl-1H-tetrazol-5-yl)-thio]methyl]-8-oxo-5-thia-1-azabicyclo[4.2.0]oct-2-ene-2-carboxylic acid, diphenylmethyl ester: NMR (CDCl3) 1.65 (s, 6H), 3.67 (broad s, 2H, C-2), 3.80 (s, 3H, N-CH3), 4.20 (m, 2H, C-3 CH2), 5.03 (d, J=5Hz, 1H, C-6), 6.0 (m, 1H, C-7), 6.75, 6.88, 6.95 (3s's, 1H each, 2 CO2CH(C6H5)2, 1 thiazole proton).

(h)
[5S-[5α,6β,7α(Z)]]-7-[[(2-Amino-4-thiazolyl)[(1-carboxyl-1-methylethoxy)imino]acetyl]amino]-3-[[(1-methyl-1H-tetrazol-5-yl)thio]methyl]-8-oxo-5-thia-1-azabicyclo[4.2.0]oct-2-ene-2-carboxylic acid 5-oxide, trifluoroacetate salt A solution of 585 mg. of the diphenylmethyl ester product from part (g) is stirred with 0.7 ml. of anisole, 5.5 ml. of dried methylene chloride, and 1.5 ml. of trifluoroacetic acid at 0° for 2.5 hours and at room temperature for one hour. The solvents are removed in vacuo and the residue is triturated with ether to yield 294 mg. of [6R-[6α,7β(Z))]]-7-[[(2-amino-4-thiazolyl)[(1-carboxyl-1-methylethoxy)imino]acetyl]amino]-3-[[(1-methyl-1H-tetrazol-5-yl)thio]methyl]-8-oxo-5-thia-1-azabicyclo[4.2.0]oct-2-ene-2-carboxylic acid, trifluoroacetate salt.

A solution of 250 mg. of this product in a mixture of 3.5 ml. of methylene chloride and 1 ml. of trifluoroacetic acid is stirred with 73 mg. of m-chloroperbenzoic acid at 0° for ten minutes. The mixture is concentrated in vacuo and triturated with ether to yield 256 mg. of [5S-[5α,6β,7α(Z)]]-7-[[(2-amino-4-thiazolyl)[(1-carboxy-1-methylethoxy)imino]acetyl]amino]-3-[[(1-methyl-1H-tetrazol-5-yl)thio]methyl]-8-oxo-5-thia-1-azabicyclo[4.2.0]oct-2-ene-2-carboxylic acid, 5-oxide, trifluoroacetate salt; m.p. 214°–218° dec. (darkens at 147°).

Anal. for $C_{21}H_{22}N_9O_{10}F_3S_3$ Calc'd: C, 35.34; H, 3.11; N, 17.67; F, 7.99; S, 13.48. Found: C, 40.07; H, 4.56; N, 15.99; F, 4.89; S, 12.35.

(i)
[5S-[5α,6β,7α(Z)]]-7-[[(2-Amino-4-thiazolyl)[(1-carboxy-1-methylethoxy)imino]acetyl]amino]-3-[[(1-methyl-1H-tetrazol-5-yl)thio]methyl]-8-oxo-5-thia-1-azabicyclo[4.2.0]oct-2-ene-2-carboxylic acid, 5-oxide, disodium salt The trifluoroacetate salt product from part (h) is treated with a molar excess of sodium bicarbonate according to the procedure of Example 1 (f) to yield [5S-[5α,6β,7α(Z)]]-7-[[(2-amino-4-thiazolyl)[(1-carboxy-1-methylethoxy)imino]acetyl]amino]-3-[[(1-methyl-1H-tetrazol-5-yl)thio]methyl]-8-oxo-5-thia-1-azabicyclo[4.2.0]oct-2-ene-2-carboxylic acid, 5-oxide, disodium salt.

EXAMPLE 3

[5S-[5α,6β,7α(Z)]]-7-[[(2-Amino-4-thiazolyl)[(1-carboxy-1-methylethoxy)imino]acetyl]amino]-3-[[(1-methyl-1H-tetrazol-5-yl)thio]methyl]-8-oxo-5-thia-1-azabicyclo[4.2.0]oct-2-ene-2-carboxylic acid, 5-oxide, disodium salt The product of Example 2 can also be prepared according to the following procedure.

(a)
[5S-[5α,6β,7α(Z)]]-7-[[(2-Amino-4-thiazolyl)[(1-diphenylmethoxycarbonyl-1-methoxyethoxy)imino]acetyl]amino]-3-[[(1-methyl-1H-tetrazol-5-yl)thio]methyl]-8-oxo-5-thia-1-azabicyclo[4.2.0]oct-2-ene-2-carboxylic acid, 5-sulfoxide, diphenylmethyl ester A solution of the diphenylmethyl ester product from Example 2(g) (93 mg., 0.1 mmole) in 2 ml. of methylene chloride is cooled to 0° and 20 mg. (0.1 mmole) of m-chloroperbenzoic acid is added. After thirty minutes the solution is washed with sodium bicarbonate solution, dried, and the solvent evaporated to yield [5S-[5α,6β,7α(Z)]]-7-[[(2-amino-4-thiazolyl)[(1-diphenylmethoxycarbonyl-1-methylethoxy)imino]acetyl]amino]-3-[[(1-methyl-1H-tetrazol-5-yl)thio]methyl]-8-oxo-5-thia-1-azabicyclo[4.2.0]oct-2-ene-2-carboxylic acid, 5sulfoxide, diphenylmethyl ester.

(b)
[5S-[5α,6β,7α(Z)]]-7-[[(2-Amino-4-thiazolyl)[(1-carboxy-1-methylethoxy)imino]acetyl]amino]-3-[[(1-methyl-1H-tetrazol-5-yl)thio]methyl]-8-oxo-5-thia-1-azabicyclo[4.2.0]oct-2-ene-2-carboxylic acid, 5-oxide, disodium salt The diphenylmethyl ester product from part (a) is treated with a mixture of trifluoroacetic acid and anisole in methylene chloride according to the procedure of Example 2(h) to yield [5S-[5α,6β,7α(Z))]]-7-[[(2-amino-4-thiazolyl)[(1-carboxy-1-methoxyethoxy)imino]acetyl]amino]-3-[[(1-methyl-1H-tetrazol-5-yl)thio]methyl]-8-oxo-5-thia-1-azabicyclo[4.2.0]oct-2-ene-2-carboxylic acid, 5-oxide, trifluoroacetate salt.

This trifluoroacetate salt product is treated with a molar excess of sodium bicarbonate according to the procedure of Example 1(f) to yield [5S-[5α,6β,7α(Z)]]-7-[[(2-amino-4-thiazolyl)[(1-carboxy-1-methylethoxy)imino]acetyl]amino]-3-[[(1-methyl-1H-tetrazol-5-yl)thio]methyl]-8-oxo-5-thia-1-azabicyclo[4.2.0]oct-2-ene-2carboxylic acid, 5-oxide, disodium salt.

EXAMPLE 4

[5S-[5α,6β,7α(Z)]]-7-[[(2-Amino-4-thiazolyl)[(1-carboxy-1-methylethoxy)imino]acetyl]amino]-3-[(aminocarbonyloxy)methyl]-8-oxo-5-thia-1-azabicyclo[4.2.0]oct-2-ene-2-carboxylic acid, 5-oxide, disodium salt (i.e., β-sulfoxide, syn isomer)

(a)
[6R-[6α,7β(Z)]]-7-[[(2-Amino-4-thiazolyl)[(1-diphenylmethoxycarbonyl-1-methylethoxy)imino]acetyl]amino]-3-(aminocarbonyloxy)methyl]-8-oxo-5-thia-1-azabicyclo[4.2.0]oct-2-ene-2-carboxylic acid, diphenylmethyl ester A solution of 417 mg. of [6R-[6α,7β]]-7-amino-3-[(aminocarbonyloxy)methyl]-8-oxo-5-thia-1-azabicyclo[4.2.0]oct-2-ene-2-carboxylic acid, diphenylmethyl ester (prepared as set forth in U.S. Pat. No. 4,138,555 and having m.p. 135°–139° from chloroform) and 417 mg. of 2-(2-amino-4-thiazolyl)-2-diphenylmethoxycarbonyl-1-methylethoxy)iminoacetic acid from Example 2(f) are stirred in 7 ml. of dimethylformamide with 146 mg. of N-hydroxybenzo triazole at 0°. A solution of 196 mg. of dicyclohexylcarbodiimide in 3 ml. of dimethylformamide is added. After 25 hours, the reaction mixture is worked up as described in Example 2(g) to yield a crude product that is purified by column chromatography on silica gel to yield 512 mg. of [6R-[6α,7β(Z)]]-7-[[(2-amino-4-thiazolyl)[(1-diphenylmethoxycarbonyl-1-methylethoxy)imino]acetyl]amino]-3-[(aminocarbonyloxy)methyl]-8-oxo-5-thia-1-azabicyclo[4.2.0]oct-2-ene-2-carboxylic acid, diphenylmethyl ester: NMR (CDCl$_3$) 1.65 (s,6H, (CH$_3$)$_2$), 3.40 (m, 2H, C-2), 4.60, 5.38 (m, 5H, C-6, C-3', NH$_2$), 6.67, 6.87, 6.93 (s's, 1H each, thiazole H plus 2 CH(C$_6$H$_5$)$_2$).

(b)
[5S-[5α,6β,7α(Z)]]-7-[[(2-Amino-4-thiazolyl)[1-diphenylmethoxycarbonyl-1-methylethoxy)imino]acetyl]amino]-3-[(aminocarbonyloxy)methyl]-8-oxo-5-thia-1-azabicyclo[4.2.0]oct-2-ene-2-carboxylic acid, 5-oxide, diphenylmethyl ester A solution of 312 mg. of the ester product from part (a) in 6 ml. of methylene chloride is cooled to 0° and a solution of 73 mg. of m-chloroperbenzoic acid in 4 ml. of methylene chloride is added. After 15 minutes, the resulting solution is washed with a mixture of dilute sodium bicarbonate solution and sodium sulfite solution, dried, and the solvents evaporated. The residue is purified by preparative TLC on silica gel to give 268 mg. of [5S-[5α,6β,7α (Z)]]-7-[[(2-amino-4-thiazolyl)[(1-diphenylmethoxycarbonyl-1-methylethoxy)imino]acetyl]amino]-3-[(aminocarbonyloxy)methyl]-8-oxo-5-thia-1-azabicyclo[4.2.0]oct-2-ene-2-carboxylic acid, 5-oxide, diphenylmethyl ester: NMR (CDCl$_3$-CD$_3$OD) 1.63 (s,6H, (CH$_3$)$_2$) 3.28 and 3.70 (d of d, 2H, J=14 Hz, C-2), 4.70 (d, 1H, J=5 Hz, C-6), 4.75 and 5.30 (d of d, 2H, J=14 Hz, C-3') 6.18 (d, 1H, J=5 Hz, C-7), 6.53, 6.83 and 6.87 (s's, 1H each, thiazole H and 2 CH(C$_6$H$_5$)$_2$).

(c)
[5S-[5α,6β,7α(Z)]]-7-[[(2-Amino-4-thiazolyl)[(1-carboxy-1-methylethoxy)imino]acetyl]amino]-3-[(aminocarbonyloxy)methyl]-8-oxo-5-thia-1-azabicyclo[4.2.0]oct-2-ene-2-carboxylic acid, 5-oxide, trifluoroacetate salt A solution of 268 mg. of the diphenylmethyl ester product from part (b) in 6 ml. of methylene chloride and 0.375 ml. of anisole is cooled to 0° and 1.5 ml. of trifluoroacetic acid is added. After 3.5 hours, the solvent is removed in vacuo and the residue is triturated with ether to yield 172 mg. of [5S-[5α,6β,7α(Z)]]-7-[[(2-amino-4-thiazolyl)[(1-carboxy-1-methylethoxy)imino]acetyl]amino]-3-[(aminocarbonyloxy)methyl]-8-oxo-5-thia-1-azabicyclo[4.2.0]oct-2-ene-2-carboxylic acid, 5-oxide, trifluoroacetate salt, m.p.>250° (R$_f$=0.21, silica gel, butanol-acetic acid-water (3:1:1)).

(d)
[5S-[5α,6β,7α(Z)]]-7-[[(2-Amino-4-thiazolyl][(1-carboxy-1-methylethoxy)imino]acetyl]amino]-3-[(aminocarbonyloxy)methyl]-8-oxo-5-thia-1-azabicyclo[4.2.0]oct-2-ene-2-carboxylic acid, 5-oxide, disodium salt The trifluoroacetate salt product from part (c) is treated with a molar excess of sodium bicarbonate according to the procedure of Example 1(f) to yield [5S-[5α,6β,7α(Z)]]-7-[[(2-amino-4-thiazolyl)[(1-carboxy-1-methylethoxy)imino]acetyl]amino]-3-[(aminocarbonyloxy)methyl]-8-oxo-5-thia-1-azabicyclo[4.2.0]oct-2-ene-2-carboxylic acid, 5-oxide, disodium salt.

EXAMPLES 5–29

Following the procedure of Examples 1, 2 and 4 but employing trifluoroacetic acid salt shown in Col. I, treatment with m-chloroperbenzoic acid yields the β-sulfoxide shown in Col. II. Further treatment with sodium bicarbonate according to the procedure of Example 1(f) yields the sodium salt shown in Col. III.

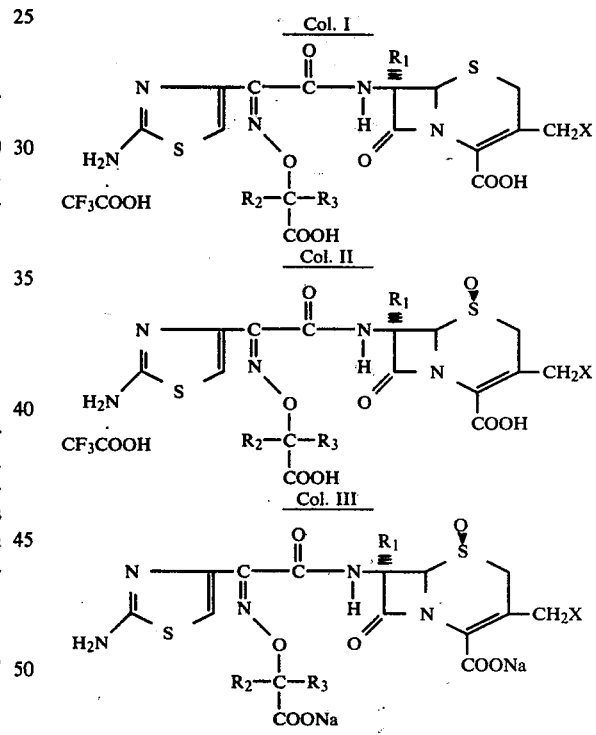

| Example | R$_1$ | X | R$_2$ | R$_3$ |
|---|---|---|---|---|
| 5 | —H | —O—C(O)—CH$_3$ | —C$_2$H$_5$ | —C$_2$H$_5$ |
| 6 | —H | —O—C(O)—CH$_3$ | —n-C$_3$H$_7$ | —n-C$_3$H$_7$ |
| 7 | —H | —H | —i-C$_3$H$_7$ | —CH$_3$ |
| 8 | —H | —O—C(O)—C$_2$H$_5$ | —CH$_3$ | —CH$_3$ |
| 9 | —H | —O—C(O)—NH$_2$ | —C$_2$H$_5$ | —CH$_3$ |

-continued

| Example | R₁ | X | R₂ | R₃ |
|---|---|---|---|---|
| 10 | —H | —O—C(=O)—NH₂ | —C₂H₅ | —C₂H₅ |
| 11 | —H | —O—C(=O)—NH₂ | —C₂H₅ | —n-C₃H₇ |
| 12 | —OCH₃ | —O—C(=O)—CH₃ | —CH₃ | —CH₃ |
| 13 | —OCH₃ | —O—C(=O)—NH₂ | —CH₃ | —CH₃ |
| 14 | —H | —S-(1,3,4-thiadiazol-2-yl with 5-CH₃) | —CH₃ | —CH₃ |
| 15 | —OCH₃ | —S-(1,3,4-thiadiazol-2-yl with 5-CH₃) | —CH₃ | —CH₃ |
| 16 | —H | —S-(1,3,4-thiadiazol-2-yl with 5-CH₃) | —C₂H₅ | —CH₃ |
| 17 | —H | —S-(1,3,4-thiadiazol-2-yl with 5-CH₃) | —C₂H₅ | —C₂H₅ |
| 18 | —H | —S-(1-methyl-1H-tetrazol-5-yl) | —C₂H₅ | —C₂H₅ |
| 19 | —OCH₃ | —S-(1-methyl-1H-tetrazol-5-yl) | —CH₃ | —CH₃ |
| 20 | —H | —S-(1-methyl-1H-tetrazol-5-yl) | —CH₃ | —C₂H₅ |
| 21 | —H | —S-(1-ethyl-1H-tetrazol-5-yl) | —CH₃ | —CH₃ |
| 22 | —H | —S-(1H-tetrazol-5-yl) | —C₂H₅ | —CH₃ |
| 23 | —H | —S-(1-CH₂COONa-1H-tetrazol-5-yl) | —CH₃ | —CH₃ |
| 24 | —OCH₃ | —S-(1-CH₂—COONa-1H-tetrazol-5-yl) | —CH₃ | —CH₃ |

-continued

| Example | $R_1$ | X | $R_2$ | $R_3$ |
|---|---|---|---|---|
| 25 | —H | —S-[tetrazole with N-(CH$_2$)$_2$—COONa] | —CH$_3$ | —C$_2$H$_5$ |
| 26 | —OCH$_3$ | —S-[tetrazole with N-CH$_2$SO$_3$Na] | —C$_2$H$_5$ | —C$_2$H$_5$ |
| 27 | —H | —S-[tetrazole with N-CH$_2$SO$_3$Na] | —CH$_3$ | —n-C$_3$H$_7$ |
| 28 | —H | —S-[tetrazole with N-(CH$_2$)$_2$SO$_3$Na] | —CH$_3$ | —CH$_3$ |
| 29 | —H | —S-[tetrazole with N-(CH$_2$)$_2$N(CH$_3$)$_2$] | —CH$_3$ | —CH$_3$ |

Of course, by substituting potassium bicarbonate for the sodium bicarbonate in the procedures of Examples 1 to 29, one obtains the corresponding potassium salt.

The compounds where $R_2$ and $R_3$ are not the same are, of course, mixtures of diostereomers due to the asymmetric carbon atom. These compounds can be obtained in the D-, L- or D,L-isomeric form depending upon the optically activity of the sulfide starting material.

The final products of Examples 5 to 29 are obtained in the syn or anti configuration depending upon the configuration of the sulfide cephalosporin starting material.

EXAMPLE 30

[5S-[5α,6β,7α(Z)]]-3-[(Acetyloxymethyl]-7-[[(2-amino-4-thiazolyl)[(1-carboxy-1-methylethoxy)imino]acetyl]amino]-8-oxo-5-thia-1-azabicyclo[4.2.0]oct-2-ene-2-carboxylic acid, 5-oxide, disodium salt The product of Example 1 can also be prepared according to the following procedure.

(a)

[5S-[5α,6β,7α]]-3-[(Acetyloxy)methyl]-7-amino-8-oxo-5-thia-1-azabicyclo[4.2.0]oct-2-ene-2-carboxylic acid, 5-oxide, diphenylmethyl ester (i.e. β-sulfoxide) and [5R-[5α,6α,7β]]-3-[(Acetyloxy)methyl]-7-amino-8-oxo-5-thia-1-azabicyclo[4.2.0]oct-2-ene-2-carboxylic acid, 5-oxide, diphenylmethyl ester (i.e. α-sulfoxide)

A slurry of 50 g. of 7-aminocephalosporanic acid (7-ACA) in 1 liter of water is stirred magnetically while t-octyl amine is added dropwise, thereby maintaining the pH between 7 and 8. After one hour, the undissolved solid is filtered (Celite) and the filtrate is treated with a solution prepared by adjusting a mixture of 10 ml. of t-octylamine and 20 ml. of water to pH 8.0 with 6 N hydrochloric acid. The resulting solution is then treated with 10 ml. of salicylaldehyde. After 2 minutes a solid forms and after 5 minutes an additional 10 ml. of salicylaldehyde is added. The slurry is stirred for an additional 10 minutes, cooled to 0° for 4.5 hours and filtered. The filter cake is slurried twice with 300 ml. of cold water and filtered. The wet cake is dried at 60° in vacuo over large amounts of P$_2$O$_5$ to give 66 g. of tan solid 7-salicylaldiminocephalosporanic acid, t-octyl amine salt.

A slurry of 25.25 g. (0.05 mole) of the above t-octyl amine salt (powdered with a mortar and pestle) in 250 ml. of dry acetonitrile is treated with 9.5 g. (0.05 mole) of p-toluenesulfonic acid monohydrate. After 10 minutes, a solution of 9.7 g. (0.05 mole) of diphenyldiazomethane in 50 ml. of acetonitrile is added over the course of 15 minutes. After one hour, the slurry is filtered, the solid is washed with acetonitrile, and the combined filtrate and washings are evaporated in vacuo. The resulting oil is chromatographed on a 300 g. silica gel column eluted with methylene chloride. Fractions (500 ml.) 2-3 contain 7.5 g. of the desired diphenylmethyl ester product plus some higher $R_f$ impurity (monitored by silica gel TLC with 3:1 chloroformethyl acetate development): fractions 4-11 contain 12.3 g. of pure 7-salicylaldiminocephalosporanic acid, diphenylmethyl ester; NMR (CDCl$_3$) δ 1.97 (s, 3H, CH$_3$CO); 3.23 and 3.60 (AB q, J=19 Hz, 2H, C-2); 4.67 and 5.01 (AB, q, J=14 Hz, 2H, C-3'); 4.99 (d, J=5 Hz, 1H, C-6); 5.20 (broadened d, J=5 Hz, 1H, C-7); 6.62-7.60 (m, about 15H); 9.07 (broad s, 1H, —CH=N—).

A solution of 12.3 g. (0.023 mole) of the above diphenylmethyl ester product in 125 ml. of methylene chloride is cooled to 0° and a solution of 4.6 g. (0.023 mole) of 85% m-chloroperbenzoic acid in 70 ml. of methylene chloride is added over the course of 15 minutes. After one hour, the slurry is washed with a mixture of 100 ml. of 5% sodium bicarbonate and 50 ml. of 6% sodium sulfite solution. The organic layer is dried and evaporated in vacuo. The resulting oil crystallizes from 70 ml. of ethyl acetate giving 8.7 g. of a mixture of α- and β-sulfoxides. A second crop of 1.5 g. of a mixture of α- and β- sulfoxides is also obtained. The major (α-) isomer has a lower field acetate methyl (2.02 ppm) and C-2 quartet (3.57 and 4.10 ppm) when compared to those of the minor (β) isomer (1.97, 3.26 and 3.94 ppm, respectively).

A slurry of 10 g. (0.018 mole) of the above 7-salicylaldimiocephalosporanic acid, diphenylmethyl ester, α- and β-sulfoxide mixture in 100 ml. of ethyl acetate is treated with 3.42 g. (0.018 mole) of p-toluenesulfonic acid monohydrate. After 5.5 hours, 300 ml. of ether is added and the gummy solid is triturated, filtered, and washed twice with ether. The moist solid is dissolved in 200 ml. of ethyl acetate and the solution is washed with 100 ml. of 5% sodium bicarbonate solution, dried, and evaporated to give 8.0 g. of residue. Chromatography on a 300 g. silica gel column eluted with 3:1 chloroform-ethyl acetate gives (500 ml. fractions): fraction 3, 1.0 g. of recovered 7-salicylaldiminocephalosporanic acid, diphenylmethyl ester; fractions 6–16, 4.5 g. of [5R-[5α,6α, 7β]]-3-[(acetyloxy)methyl]-7-amino-8-oxo-5-thia-1-azabicyclo[4.2.0]oct-2-ene-2-carboxylic acid, 5-oxide, diphenyl ester (i.e. α-sulfoxide isomer): NMR (CDCl₃) δ 2.00 (CH₃COO-); 3.43 and 4.06 ppm (AB q, C-2); fraction 22–30 (eluant is changed to ethyl acetate after fraction 16) 1.5 g. of [5S-[5α,6β, 7α]]-3-[(acetyloxy)methyl]-7-amino-8-oxo-5-thia-1-azabicyclo[4.2.0]oct-2-ene-2-carboxylic acid, 5-oxide, diphenylmethyl ester (i.e., β-sulfoxide isomer): NMR (CDCl₃) δ 2.10 (CH₃COO—); 2.97 and 3.54 ppm (AB q, C-2).

(b)
[5S-[5α,6β,7α(Z)]]-3-[(Acetyloxy)methyl]-7-[[(2-amino-4-thiazolyl)[(1-diphenylmethoxycarbonyl-1-methylethoxy)imino]acetyl]amino]-8-oxo-5-thia-1-azabicyclo[4.2.0]oct-2-ene-2-carboxylic acid, 5-oxide, diphenylmethyl ester The iminoacetic acid hydrochloride salt product of Example 2(e) (230 mg., 1 mmole) and the β-sulfoxide diphenylmethyl ester from part (a) (454 mg., 1 mmole) are dissolved in 3 ml. of dry dimethylformamide. A solution of dicyclohexylcarbodiimide (206 mg., 1 mmole) in 4.5 ml. of anhydrous tetrahydrofuran is added to the mixture. After stirring at room temperature for 9 hours, the mixture is allowed to stand at 0°–5° overnight. Precipitated dicyclohexylurea is removed by filtration and the filtrate is concentrated in vacuo at 40°. The residue is dissolved in ethyl acetate, washed with saturated sodium bicarbonate solution and then water, and finally dried (Na₂SO₄). Removal of the solvent under reduced pressure yields a residue which is purified by chromatography on silica gel to yield as a foam [5S-[5α,6β,7α(Z)]]-3-[(acetyloxy)methyl]-7-[[(2-amino-4-thiazolyl)[(1-diphenylmethoxycarbonyl-1-methylethoxy)imino]acetyl]amino]-8-oxo-5-thia-1-azabicyclo[4.2.0]oct-2-ene-2-carboxylic acid, 5-oxide, diphenylmethyl ester.

(c)
[5S-[5α,6β,7α(Z)]]-3-[(Acetyloxy)methyl]-7-[[(2-amino-4-thiazolyl)[(1-carboxy-1-methylethoxy)imino]acetyl]amino]-8-oxo-5-thia-1-azabicyclo[4.2.0]oct-2-ene-2-carboxylic acid, 5-oxide, disodium salt The diphenylmethyl ester product from part (b) is treated with anisole and trifluoroacetic acid as set forth in Example 2(h) to remove the diphenylmethyl ester groups and yield [5S-[5α,6β,7α(Z)]]-3-[(acetyloxy)methyl]-7-[[(2-amino-4-thiazolyl)[(1-carboxy-1-methylethoxy)imino]acetyl]amino]-8-oxo-5-thia-1-azabicyclo[4.2.0]oct-2-ene-2-carboxylic acid, 5-oxide, trifluoroacetate salt.

This trifluoroacetate salt is then treated with a molar excess of sodium bicarbonate according to the procedure of Example 1(f) to yield [5S-[5α, 6β,7α(Z)]]-3-[(acetyloxy)methyl]-7-[[(2-amino-4-thiazolyl)[(1-carboxy-1-methylethoxy)imino]acetylamino]-8-oxo-5-thia-1-azabicyclo[4.2.0]oct-2-ene-2-carboxylic acid, 5-oxide, disodium salt.

EXAMPLE 31

[5R-[5α,6α,7β(Z)]]-3-[(Acetyloxy)methyl]-7-[[(2-amino-4-thiazolyl)[(1-carboxy-1-methylethoxy)imino]acetyl]amino]-8-oxo-5-thia-1-azabicyclo[4.2.0]oct-2-ene-2-carboxylic acid, 5-oxide, disodium salt [i.e., α-sulfoxide, syn isomer (a)
[5R-[5α,6α,7β(Z)]]-3-[(Acetyloxy)methyl]-7-[[(2-amino-4-thiazolyl)[(1-diphenylmethoxycarbonyl-1-methylethoxy)imino]acetyl]amino]-8-oxo-5-thia-1-azabicyclo[4.2.0]oct-2-ene-2-carboxylic acid, 5-oxide, diphenylmethyl ester A cold solution of 476 mg. (1 mmole) of the iminoacetic acid hydrochloride salt product of Example 2(e), 0.159 ml. (1 mmole) of diethylaniline, 227 mg. (1 mmole) of dicyclohexylcarbodiimide, and 153 mg. (1 mmole) of N-hydroxybenzotriazole in 10 ml. of dimethylformamide is stirred for one hour and then 454 mg. (1 mmole) of the α-sulfoxide diphenylmethyl ester from Example 30(a) is added. After stirring at room temperature for 4 hours, the reaction mixture is concentrated to about 1 ml., diluted with 150 ml. of ethyl acetate, washed three times with 100 ml. of 0.5 N HCl, washed with saturated NaCl, dried over Na₂SO₄, and evaporated to dryness to yield 550 mg. of crude product. Purification by chromatography yields 218 mg. of [5R-[5α,6α,7β(Z)]]-3-[(acetyloxy)methyl]-7-[[(2-amino-4-thiazolyl)[(1-diphenylmethoxycarbonyl-1-methylethoxy)imino]acetyl]amino]-8-oxo-5-thia-1-azabicyclo[4.2.0]oct-2-ene-2-carboxylic acid, 5-oxide, diphenylmethyl ester: NMR (CDCl₃) 1.65 and 1.70 (s's, 3H, (CH₃)₂C), 2.03 (s, 3H, CH₃CO), 3.83 (2H, d of d, J=17 Hz, C-2), 4.60 (1H, d, J=5 Hz, C-6), 5.03 (2H, d of d, J=14 Hz, C-3CH₂), 5.50 (1H, m, C-7), 6.83, 6.91, 7.03 (s's, 2 CH(C₆H₅)₂, and 1 thiazole H).

(b)
[5R-[5α,6α,7β(Z)]]-3-[(Acetyloxy)methyl]-7-[[(2-amino-4-thiazolyl)[(1-carboxy-1-methylethoxy)imino]acetyl]amino]-8-oxo-5-thia-1-azabicyclo[4.2.0]oct-2-ene-2-carboxylic acid, 5-oxide, trifluoroacetate salt A solution of 217 mg. of the diphenylmethyl ester product from part (a), 0.25 ml. of anisole, 2 ml. of methylene chloride, and 0.5 ml. of trifluoroacetic acid is stirred for 1.5 hours at 0° and 30 minutes at room temperature. The solvents are removed in vacuo and the residue is triturated with hexane-ether and dried to give 151 mg. of [5R-[5α,6α,7β(Z)]]-3-[(acetyloxy)methyl]-7-[[(2-amino-4-thiazolyl)[(1-carboxy-1-methylethoxy)imino]acetyl]amino]-8-oxo-5-thia-1-azabicyclo[4.2.0]oct-2-ene-2-carboxylic acid, 5-oxide, trifluoroacetate salt: NMR (CDCl₃–CD₃OD) 1.63 and 1.68 (s's, 3H, (CH₃)₂C), 2.10 (s, 3H, CH₃CO), 4.87 (1H, d, J=5 Hz, C-6), 5.70 (1H, d, J=5 Hz, C-7), 7.03 (s, 1H, 1 thiazole H).

(c)

[5R-[5α,6α,7β(Z)]]-3-[(Acetyloxy)methyl]-7-[[(2-amino-4-thiazolyl)[(1-carboxy-1-methylethoxy)imino]acetyl]amino]-8-oxo-5-thia-1-azabicyclo[4.2.0]oct-2-ene-2-carboxylic acid, 5-oxide, disodium salt The trifluoroacetate salt product from part (b) is treated with a molar excess of sodium bicarbonate according to the procedure of Example 1(f) to yield [5R-[5α,6α,7β(Z)]]-3-[(acetyloxy)methyl]-7-[[(2-amino-4-thiazolyl)[(1-carboxy-1-methylethoxy)imino]acetyl]amino]-8-oxo-5-thia-1-azabicyclo[4.2.0]oct-2-ene-2-carboxylic acid, 5-oxide, disodium salt.

EXAMPLES 32–42

Following the procedures of Examples 30 and 31 but employing the 7-aminocephalosporanic acid ester sulfoxide shown in Col. I and the iminoacetic ester shown in Col. II, one obtains the acylated ester product shown in Col. III. Removal of the ester protecting groups yields the acid shown in Col. IV which can then be converted to the sodium or potassium salt forms.

Col. I

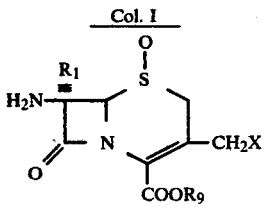

Col. II

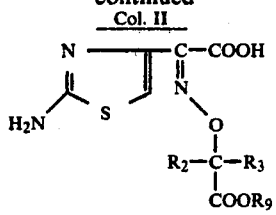

Col. III

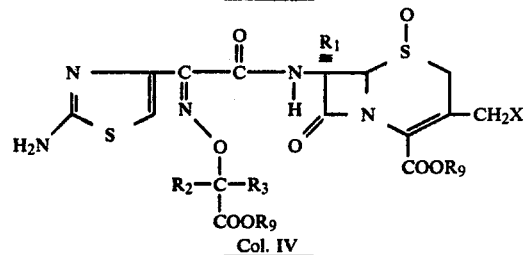

Col. IV

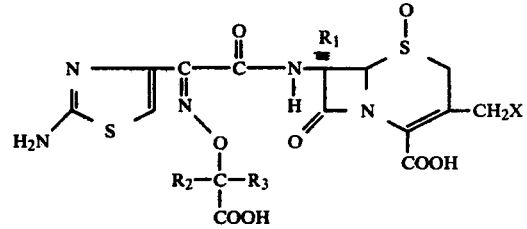

| Example | R₁ | X | R₉ | R₂ | R₃ |
|---|---|---|---|---|---|
| 32 | —H | —O—C(O)—CH₃ | —CH(C₆H₅)₂ | —C₂H₅ | —C₂H₅ |
| 33 | —H | —O—C(O)—CH₃ | —CH(C₆H₅)₂ | —CH₃ | —n-C₃H₇ |
| 34 | —OCH₃ | —O—C(O)—CH₃ | —CH(C₆H₅)₂ | —CH₃ | —CH₃ |
| 35 | —H | —S-(1-methyltetrazol... N=N,N-CH₃) | —C—(CH₃)₃ | —CH₃ | —CH₃ |
| 36 | —H | —S-(1-methyltetrazolyl) | —CH₂—C₆H₄—OCH₃ | —C₂H₅ | —C₂H₅ |
| 37 | —H | —S-(1-methyltetrazolyl) | —CH(C₆H₅)₂ | —CH₃ | —C₂H₅ |

-continued

| Example | R₁ | X | R₉ | R₂ | R₃ |
|---|---|---|---|---|---|
| 38 | —H | -S-(4-methylthiazol-2-yl) | —CH(C₆H₅)₂ | —CH₃ | —CH₃ |
| 39 | —H | -S-(1-carboxymethyl-1H-tetrazol-5-yl) | —CH(C₆H₅)₂ | —CH₃ | —CH₃ |
| 40 | —H | -S-(1-sulfomethyl-1H-tetrazol-5-yl) | —CH(C₆H₅)₂ | —CH₃ | —C₂H₅ |
| 41 | —H | —O—C(=O)—NH₂ | —C—(CH₃)₃ | —CH₃ | —i-C₃H₇ |
| 42 | —H | —O—C(=O)—NH₂ | —CH(C₆H₅)₂ | —C₂H₅ | —C₂H₅ |

The products of Examples 32 to 42 are obtained as the α- or β- sulfoxide depending upon the configuration of the sulfoxide group in the starting material of Col. I and as the syn of anti isomer depending upon the configuration of the iminoacetic acid shown in Col. II.

Also, the compounds where R₂ and R₃ are not the same are, of course, optically active due to the asymmetric carbon atom. These compounds can be obtained in the D-, L-, or D,L-isomeric form depending upon the optical activity of the iminoacetic acid of Col. II.

EXAMPLE 43

[5S-[5α,6β,7α(Z)]]-3-[[4-(Aminocarbonyl)pyridino]methyl]-7-[[(2-amino-4-thiazolyl)[(1-carboxy-1-methylethoxy)imino]acetyl]amino]-8-oxo-5-thia-1-azabicyclo[4.2.0]oct-2-ene-2-carboxylic acid, 5-oxide (i.e., β-sulfoxide, syn isomer)

A mixture of 0.005 mole of the disodium salt product of Example 1, 0.0075 mole of 4-pyridinecarboximide, 12 g. of potassium thiocyanate, and 7.5 ml. of water are heated at 50° for 24 hours. The resulting solution is passed through a chromatography column filled with the ion exchange Amberlite XAD-2. The column is washed with water and the titled compound is eluted with a mixture of water:methanol (8:2). The methanol is evaporated from the eluate and the aqueous solution is lyophilized. The amorphous residue is triturated with ether and filtered under suction to yield [5S-[5α,-6β,7α(Z)]]-3-[[4-(aminocarbonyl)pyridino]methyl]-7-[[(2-amino-4-thiazolyl)[(1-carboxy-1-methylethoxy)imino]acetyl]amino]-8-oxo-5-thia-1-azabicyclo[4.2.-0]oct-2-ene-2-carboxylic acid, 5-oxide.

Similarly, by employing the disodium salt product of Example 31 in the above procedure the corresponding α-sulfoxide product is obtained.

EXAMPLES 44-51

Following the procedure of Example 43 but employing the cephalosporanic acid disodium salt shown in Col. I and the pyridine compound shown in Col. II, one obtains the product shown in Col. III.

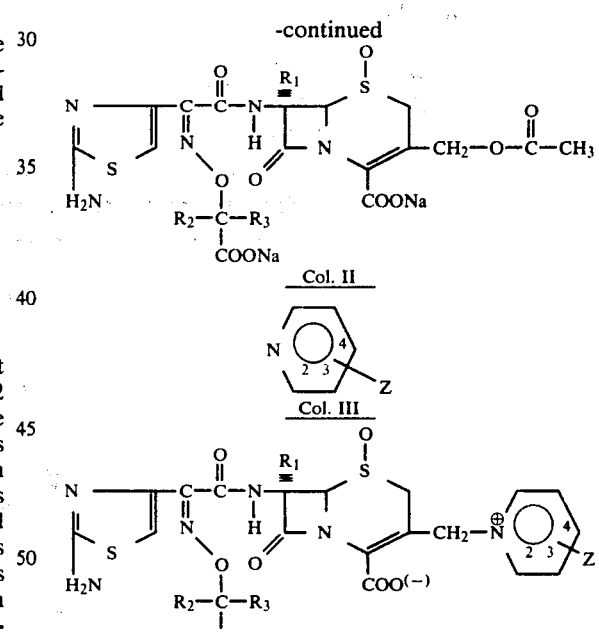

| Ex. | R₁ | R₂ | R₃ | Z |
|---|---|---|---|---|
| 44 | —OCH₃ | —CH₃ | —CH₃ | —H |
| 45 | —H | —CH₃ | —CH₃ | —CNH₃ (3) |
| 46 | —H | —CH₃ | —CH₃ | —H |
| 47 | —H | —C₂H₅ | —C₂H₅ | —CNH₂ (4) |
| 48 | —H | —CH₃ | —C₂H₅ | —CNH₂ (2) |
| 49 | —H | —CH₃ | —C₂H₅ | —CNH₂ (4) |

| Ex. | R₁ | R₂ | R₃ | Z |
|-----|-----|-----|-----|-----|
| 50 | —H | —C₂H₅ | —C₂H₅ | —H |
| 51 | —H | —n-C₃H₇ | —n-C₃H₇ | $-\overset{O}{\underset{\|}{C}}NH_2$ (4) |

The products of Examples 44 to 51 are obtained as the α- or β-sulfoxide and in the syn or anti configuration depending upon the configuration of the 3-acetoxymethyl starting material shown in Col. I. Also, when R₂ and R₃ are not the same, the products are obtained in the D-, L- or D,L-isomeric form depending upon the optical activity of the starting material shown in Col. I.

EXAMPLE 52

[5R-[5α,6α,7β(Z)]]-7-[[(2-Amino-4-thiazolyl)[(1-carboxy-1-methylethoxy)imino]acetyl]amino]-3-[[(1-methyl-1H-tetrazol-5-yl)thio]methyl]-8-oxo-5-thia-1-azabicyclo[4.2.0]oct-2-ene-2-carboxylic acid, 5-oxide, disodium salt (i.e., α-sulfoxide, syn isomer)

0.002 mole of the disodium salt product of Example 31 is brought into solution in 100 ml. of a phosphate buffer at a pH of 6.4. Then 0.0024 mole of 1-methyl-1H-tetrazolyl-2-thiol is added. The solution is heated at 60° for six hours. After cooling, the pH is adjusted to 7.0 and the solution is chromatographed on the ion exchange resin Amberlite XAD-2. The fraction containing the desired product is freeze dried to yield [5R-[5 α,6α,7β(Z)]]-7-[[(2-amino-4-thiazolyl)[(1-carboxy-1-methylethoxy)imino]acetyl]amino]-3-[[(1-methyl-1H-tetrazol-5-yl)thio]methyl]-8-oxo-5-thia-1-azabicyclo[4.2.0]oct-2-ene-2-carboxylic acid, 5-oxide, disodium salt.

Similarly, by employing the disodium salt product of Example 30 in the above procedure the β-sulfoxide product of Example 2 is obtained.

EXAMPLES 53–61

Following the procedure of Example 52 but employing the cephalosporanic acid disodium salt shown in Col. 1 and the thiol shown in Col. II, one obtains the product shown in Col. III.

| Ex. | R₁ | R₂ | R₃ | hetero |
|-----|-----|-----|-----|--------|
| 53 | —H | —C₂H₅ | —C₂H₅ | tetrazole, N—CH₃ |
| 54 | —OCH₃ | —CH₃ | —CH₃ | tetrazole, N—CH₃ |
| 55 | —OCH₃ | —C₂H₅ | —C₂H₅ | thiadiazole, —CH₃ |
| 56 | —H | —CH₃ | —CH₃ | tetrazole, N—CH₂COONa |
| 57 | —H | —CH₃ | —C₂H₅ | tetrazole, N—CH₂COONa |
| 58 | —H | —C₂H₅ | —C₂H₅ | tetrazole, N—CH₂SO₃Na |
| 59 | —OCH₃ | —CH₃ | —CH₃ | tetrazole, N—CH₂SO₃Na |
| 60 | —H | —CH₃ | —n-C₃H₇ | tetrazole, N—(CH₂)₂N(CH₃)₂ |

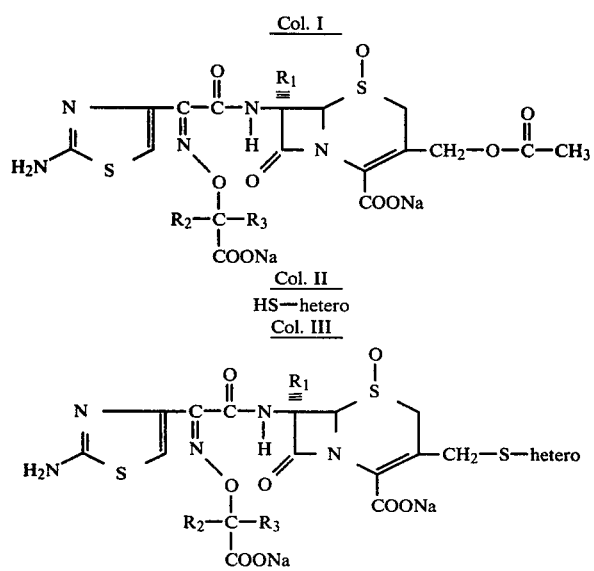

-continued

| Ex. | R₁ | R₂ | R₃ | hetero |
|---|---|---|---|---|
| 61 | —OCH₃ | —CH₃ | —CH₃ | 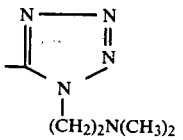 |

The products of Examples 53 to 61 are obtained as the α- or β-sulfoxide and in the syn or anti configuration depending upon the configuration of the 3-acetoxymethyl starting material shown in Col. I. Also, when $R_2$ and $R_3$ are not the same, the products are obtained in the D-, L- or D,L-isomeric form depending upon the optical activity of the starting material shown in Col. I.

What is claimed is:

1. A compound of the formula:

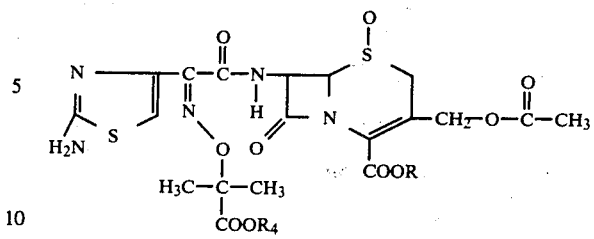

including its imino tautomeric form wherein the

group is in the syn configuration; the sulfoxide is in the β-configuration; R is hydrogen, sodium or potassium; and $R_4$ is hydrogen, sodium or potassium.

2. The compound of claim 1, [5S-[5α,6β,7α-(Z)]]-3-[(acetyloxy)methyl]-7-[[(2-amino-4-thiazolyl)[(1-carboxy-1-methylethoxy)imino]acetyl]amino]-8-oxo-5-thia-1-azabicyclo[4.2.0]oct-2-ene-2-carboxylic acid, 5-oxide.

3. The disodium salt of the compound of claim 2.

4. An antibacterial pharmaceutical composition comprising a pharmaceutically acceptable carrier and one or more antibacterially active compounds of claim 1.

5. The method of combating infections in mammals caused by gram-negative microorganisms which comprises parenterally administering an effective amount of the composition of claim 4.

* * * * *